United States Patent
Brac De La Perriere et al.

(10) Patent No.: US 10,517,811 B2
(45) Date of Patent: Dec. 31, 2019

(54) COMPOSITION COMPRISING AT LEAST ONE ANIONIC ASSOCIATIVE POLYMER, AT LEAST ONE ANIONIC FIXING POLYMER AND AT LEAST ONE STARCH

(71) Applicant: L'OREAL, Paris (FR)

(72) Inventors: Anne-Sophie Brac De La Perriere, Asnieres-sur-Seine (FR); Audrey Gilles, Clichy (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/100,788

(22) PCT Filed: Dec. 2, 2014

(86) PCT No.: PCT/EP2014/076254
§ 371 (c)(1),
(2) Date: Jun. 1, 2016

(87) PCT Pub. No.: WO2015/082470
PCT Pub. Date: Jun. 11, 2015

(65) Prior Publication Data
US 2016/0367467 A1 Dec. 22, 2016

(30) Foreign Application Priority Data

Dec. 2, 2013 (FR) .................................... 13 61947

(51) Int. Cl.
| | | |
|---|---|---|
| *A61K 8/81* | (2006.01) | |
| *A61Q 5/06* | (2006.01) | |
| *A61K 8/73* | (2006.01) | |
| *A61K 8/86* | (2006.01) | |

(52) U.S. Cl.
CPC ............ *A61K 8/8152* (2013.01); *A61K 8/732* (2013.01); *A61K 8/86* (2013.01); *A61Q 5/06* (2013.01); *A61K 2800/548* (2013.01); *A61K 2800/5424* (2013.01); *A61K 2800/594* (2013.01)

(58) Field of Classification Search
CPC ........ A61K 8/8152; A61K 8/37; A61K 8/046; A61K 8/31; A61K 8/731; A61K 8/8182
See application file for complete search history.

(56) References Cited

U.S. PATENT DOCUMENTS

| | | |
|---|---|---|
| 3,589,978 A | 6/1971 | Kamal et al. |
| 3,910,862 A | 10/1975 | Barabas et al. |
| 4,017,460 A | 4/1977 | Tessler |
| 4,031,307 A | 6/1977 | DeMartino et al. |
| 4,131,576 A | 12/1978 | Iovine et al. |
| 4,137,180 A | 1/1979 | Naik et al. |
| 4,165,367 A | 8/1979 | Chakrabarti |
| 4,223,009 A | 9/1980 | Chakrabarti |
| 4,874,554 A | 10/1989 | Lange et al. |
| 5,455,340 A | 10/1995 | Bernard et al. |
| 2011/0135589 A1 | 6/2011 | Knappe et al. |
| 2012/0064023 A1 | 3/2012 | Knappe et al. |
| 2012/0201774 A1* | 8/2012 | Schweinsberg ........ A61K 8/042 424/70.13 |
| 2012/0207692 A1* | 8/2012 | Mueller ................. A61K 8/046 424/70.13 |
| 2014/0093467 A1* | 4/2014 | Knappe ................. A61K 8/8152 424/70.15 |
| 2014/0369947 A1 | 12/2014 | Plos et al. |
| 2015/0335566 A1 | 11/2015 | Knappe et al. |

FOREIGN PATENT DOCUMENTS

| | | | |
|---|---|---|---|
| DE | 102008038105 A1 | 2/2010 | |
| DE | 102009001978 A1 | 10/2010 | |
| DE | 102011077364 A1 * | 12/2012 | ........... A61K 8/8152 |
| DE | 102011077364 A1 | 12/2012 | |
| EP | 0080976 A1 | 6/1983 | |
| FR | 2077143 A | 10/1971 | |
| FR | 2393573 A1 | 1/1979 | |
| FR | 2984135 A1 | 6/2013 | |
| WO | 2008/098717 A2 | 8/2008 | |
| WO | 2015/082471 A1 | 6/2015 | |

OTHER PUBLICATIONS

International Search Report for PCT/EP2014/076254, dated Mar. 10, 2015.
International Search Report for PCT/EP2014/076258, dated Mar. 10, 2015.
English language abstract for EP 0080976 (Jun. 8, 1983).
Porter, M.R., "Handbook of Surfactants," published by Blackie & Son (Glasgow and London), 1991, pp. 116-178.
Non-Final Office Action for copending U.S. Appl. No. 15/100,796, dated Dec. 1, 2017.
Final Office Action for copending U.S. Appl. No. 15/100,796, dated Jun. 6, 2018.
Non-Final Office Action for copending U.S. Appl. No. 15/100,796, dated Jan. 15, 2019.
Final Office Action for co-pending U.S. Appl. No. 15/100,796, dated Oct. 9, 2019.

* cited by examiner

*Primary Examiner* — Micah Paul Young
(74) *Attorney, Agent, or Firm* — The Marbury Law Group, PLLC

(57) ABSTRACT

The present invention relates to a composition comprising one or more particular anionic associative polymers, one or more particular anionic fixing polymers and one or more starches or modified starches. The present invention also relates to the use of the abovementioned composition for styling keratin fibres, preferably the hair. Finally, the invention relates to a process for treating keratin fibres, preferably the hair, using the abovementioned composition.

12 Claims, No Drawings

COMPOSITION COMPRISING AT LEAST ONE ANIONIC ASSOCIATIVE POLYMER, AT LEAST ONE ANIONIC FIXING POLYMER AND AT LEAST ONE STARCH

CROSS REFERENCE TO RELATED APPLICATIONS

This is a national stage application of PCT/EP2014/076254, filed internationally on Dec. 2, 2014, which claims priority to French Application No. 1361947, filed on Dec. 2, 2013, both of which are incorporated by reference herein in their entireties.

The present invention relates to a composition comprising one or more particular anionic associative polymers, one or more particular anionic fixing polymers and one or more starches or modified starches.

The present invention also relates to the use of the abovementioned composition for styling keratin fibres, preferably the hair.

Finally, the invention relates to a process for treating keratin fibres, preferably the hair, using the abovementioned composition.

Styling products are usually used to construct and structure the hairstyle and to give it long-lasting hold. These compositions generally comprise one or more fixing film-forming polymers, in a cosmetically acceptable medium. These polymers allow the formation of a coating film on the hair, thus providing form retention of the hairstyle.

Styling products are generally in the form of lacquers, foams or gels.

In particular, styling gels are often used in order to obtain strong fixing of the hairstyle.

Styling gels are solutions of one or more fixing film-forming polymers, thickened or gelled with one or more thickening polymers.

These thickening polymers are introduced in an attempt to give the composition good working qualities such as easy uptake in the hands, better distribution and good spreading on the hair.

However, the strong-fixing styling gels of the prior art generally have several drawbacks, such as having an uptake in the hands that is still not optimal, leaving substantial unsightly residues visible on the user's hair, scalp and/or clothes, which may give the impression that the user has dandruff, and giving insufficient fixing and also insufficient hold of the hairstyle over time.

There is thus a need to formulate a composition, especially a strong-fixing styling composition, which leaves little or no residues on the user's hair, scalp and/or clothes, while at the same time affording improved working qualities and also high styling performance, especially in terms of durability of the hair shaping.

It has now been discovered that the combination of one or more particular anionic associative polymers, one or more particular anionic fixing polymers and one or more starches or modified starches makes it possible to obtain a hair composition that has improved working qualities, high styling performance and a marked decrease in residues on the hair throughout its use.

One subject of the present invention is thus especially a composition comprising:
i) one or more anionic associative polymers,
ii) one or more anionic fixing polymers,
iii) one or more starches or modified starches, the said anionic associative polymer(s) comprising at least one unit of formula (I) and at least one unit of formula (II) below:

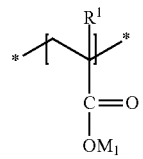

(I)

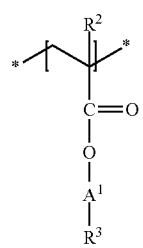

(II)

with $R^1$ and $R^2$, independently of each other, representing a hydrogen atom or a methyl group, $R^3$ representing a $C_8$-$C_{30}$ alkyl radical, $M_1$ representing a hydrogen atom or a physiologically acceptable cation, $A^1$ representing a group —$(CH_2CH_2O)_x$—, x being an integer ranging from 5 to 35, a group —$(CH_2CHMeO)_y$—, y being an integer ranging from 5 to 35, or a group —$(CH_2CH_2O)_x$—$(CH_2CHMeO)_y$—, the sum x+y being an integer ranging from 5 to 35 with x and y being greater than 0, and the said anionic fixing polymer(s) comprising at least one unit of formula (III) and at least one unit of formula (IV) below:

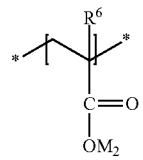

(III)

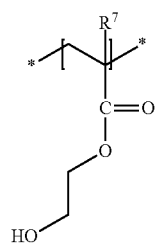

(IV)

with $R^6$ and $R^7$, independently of each other, representing a hydrogen atom or a methyl group, and $M_2$ representing a hydrogen atom or a physiologically acceptable cation.

The composition according to the invention has improved working qualities, and especially easy uptake in the hands and better distribution and good spreading of the composition on the hair.

The composition according to the invention also has high styling performance, and in particular great fixing power and long-lasting hold of the hairstyle treated with this composition.

Finally, the composition according to the invention leaves less residue on the surface of the hair during its use.

A subject of the present invention is also the use of the abovementioned composition for styling keratin fibres, preferably the hair.

Finally, a subject of the invention is a process for treating keratin fibres, preferably the hair, comprising the application of the abovementioned composition to the keratin fibres.

Other subjects, characteristics, aspects and advantages of the invention will emerge even more clearly on reading the description and the examples that follow.

In that which follows, and unless otherwise indicated, the limits of a range of values are included within this range, in particular in the expressions "of between" and "ranging from . . . to . . . ".

In addition, the expression "at least one" is equivalent to the expression "one or more".

For the purposes of the present invention, the term "associative polymer" means an amphiphilic polymer that is capable, in an aqueous medium, of reversibly combining with itself or with other molecules. It generally comprises, in its chemical structure, at least one hydrophilic region or group and at least one hydrophobic region or group.

For the purposes of the present invention, the term "hydrophobic group" means a group or a polymer bearing a saturated or unsaturated and linear or branched hydrocarbon-based chain.

When it denotes a hydrocarbon-based group, the hydrophobic group comprises at least 8 carbon atoms, preferably from 10 to 30 carbon atoms, in particular from 12 to 30 carbon atoms and preferentially from 18 to 30 carbon atoms. Preferentially, the hydrocarbon-based hydrophobic group originates from a monofunctional compound. By way of example, the hydrophobic group may be derived from a fatty alcohol, such as stearyl alcohol, dodecyl alcohol or decyl alcohol, or else from a polyalkylenated fatty alcohol, such as Steareth-100.

It may also denote a hydrocarbon-based polymer, for instance polybutadiene.

For the purposes of the present invention, the term "fixing polymer" means a polymer that is capable of giving a head of hair a shape and/or of holding the head of hair in a given shape.

As explained previously, the composition according to the invention comprises one or more particular anionic associative polymers (i) comprising at least one unit of formula (I) and at least one unit of formula (II) below:

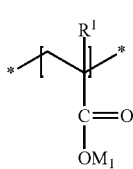

(I)

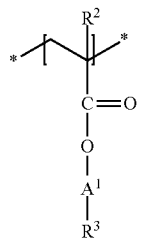

(II)

with $R^1$ and $R^2$, independently of each other, representing a hydrogen atom or a methyl group, $R^3$ representing a $C_8$-$C_{30}$ alkyl radical, $M_1$ representing a hydrogen atom or a physiologically acceptable cation, and $A^1$ representing a group —$(CH_2CH_2O)_x$—, x being an integer ranging from 5 to 35, a group —$(CH_2CHMeO)_y$—, y being an integer ranging from 5 to 35, or a group —$(CH_2CH_2O)_x$—$(CH_2CHMeO)_y$—, the sum x+y being an integer ranging from 5 to 35 with x and y being greater than 0.

As $C_8$ to $C_{30}$ alkyl radical according to the invention, mention may be made especially of the following radicals: octyl (capryl), decyl (caprinyl), dodecyl (lauryl), tetradecyl (myristyl), hexadecyl (cetyl), octadecyl (stearyl), eicosyl (arachidyl) and docosyl (behenyl).

In the above formulae and in all the following formulae, a chemical bond indicated by the symbol * corresponds to a free valency of the structural fragment in question.

As physiologically acceptable cation in formula (I) above and also in the other formulae of the description, mention may be made especially of cations of the physiologically acceptable metals of groups Ia, Ib, IIa, IIb, IIIb, VIa and VIII of the Periodic Table of the Elements, ions of ammonium type and cationic organic compounds comprising a quaternized nitrogen atom. The latter are formed, for example, by protonation, using an acid, of a primary, secondary or tertiary organic amine, or by permanent quaternization of such organic amines. Examples of these organic cationic ammonium compounds are 2-ammonioethanol and 2-trimethylammonioethanol.

Preferably, the physiologically acceptable cation in formula (I) above and in the other formulae of the description is chosen from a sodium ion and an ion derived from an alkanolamine.

Preferably, $M_1$ represents a hydrogen atom, a sodium ion or an ion derived from an alkanolamine.

In a first embodiment of the invention, the anionic associative polymer(s) that may be used in the composition according to the invention are chosen from those in which, in formula (II), $A^1$ represents a group of formula —$(CH_2CH_2O)_x$—, x being an integer ranging from 5 to 35 and in particular ranging from 10 to 24.

In a second embodiment of the invention, the anionic associative polymer(s) comprise a unit of formula (II) above in which $R^3$ represents a $C_{12}$-$C_{20}$ alkyl radical.

In a third embodiment of the invention, the anionic associative polymer(s) that may be used in the composition according to the invention are chosen from those in which, in formula (II), $R^2$ represents a methyl group.

In a fourth embodiment of the invention, the anionic associative polymer(s) comprise at least one unit of formula (I) as defined above and at least one unit of formula (II') below:

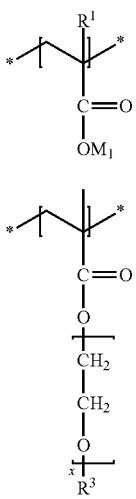

with $R^1$ representing a hydrogen atom or a methyl group, $M_1$ representing a hydrogen atom or a physiologically acceptable cation, $R^3$ representing a $C_8$ to $C_{30}$ alkyl radical and x being an integer ranging from 5 to 35 and preferably ranging from 10 to 24.

Preferably, in the composition according to the invention, the anionic associative polymer(s) are crosslinked.

For the purposes of the invention, the terms "crosslinked" and "crosslinking" should be understood as meaning the interconnection of the polymer chains via covalent chemical bonds, with formation of a network. This covalent connection of the polymer chains may be performed via direct covalent bonds or by means of molecular fragments forming bridges between the polymer chains. Such a molecular fragment is linked via a covalent chemical bond to each of the polymer chains between which it forms a bridge. For the purposes of the invention, the term "non-crosslinked" should be understood as meaning the absence of any "crosslinking" as defined above.

Crosslinking of the anionic associative polymer(s) is generally performed using at least one crosslinking agent.

The crosslinking agent(s) may be chosen especially from polyunsaturated aromatic compounds such as divinylbenzenes, divinylnaphthalenes and trivinylbenzenes, polyunsaturated alicyclic compounds such as 1,2,4-trivinylcyclohexane, phthalic acid diesters such as diallyl phthalate, polyunsaturated aliphatic compounds such as dienes, trienes and tetraenes, for instance isoprene, 1,3-butadiene, 1,5-hexadiene, 1,5,9-decatriene, 1,9-decadiene and 1,5-heptadiene, polyalkenyl ethers such as triallylpentaerythritol, diallylpentaerythritol, diallylsaccharose, octaallylsaccharose and trimethylolpropane diallyl ether, polyunsaturated esters of polyols or of polyacids such as 1,6-hexanediol di(meth)acrylate, tetramethylolmethane tri(meth)acrylate, allyl acrylate, diallyl itaconate, diallyl fumarate, diallyl maleate, trimethylolpropane tri(meth)acrylate, trimethylolpropane di(meth)acrylate and polyethylene glycol di(meth)acrylate such as ethylene glycol di(meth)acrylate, diethylene glycol di(meth)acrylate and triethylene glycol di(meth)acrylate, alkylenebisacrylamides such as methylenebisacrylamide and propylenebisacrylamide, hydroxyl or carboxyl derivatives of methylenebisacrylamide such as N,N'-bis(methylol) methylenebisacrylamide, polyunsaturated silanes such as dimethyldivinylsilane, methyltrivinylsilane, allyldimethylvinylsilane, diallyldimethylsilane and tetravinylsilane, N-methylolacrylamide, N-alkoxy(meth)acrylamides in which the alkoxy group is a $C_1$-$C_{18}$ alkoxy group, hydrolysable unsaturated silanes such as triethoxyvinylsilane, triisopropoxyvinylsilane and 3-(triethoxysilyl)propyl methacrylate, hydrolysable silanes such as ethyltriethoxysilane and ethyltrimethoxysilane, hydrolysable silanes bearing an epoxy substituent such as [2-(3,4-epoxycyclohexyl)ethyl] triethoxysilane and (3-glycidyloxypropyl)trimethoxysilane, polyisocyanates such as butane 1,4-diisocyanate, hexane 1,6-diisocyanate, phenylene 1,4-diisocyanate and 4,4'-oxybis(phenyl isocyanate), unsaturated epoxides such as glycidyl methacrylate and allyl glycidyl ether, polyepoxides such as 1,2,5,6-diepoxyhexane, diglycidyl ether and ethylene glycol diglycidyl ether, ethoxylated polyols such as diols, triols or diphenols, in each case ethoxylated with 2 to 100 mol of ethylene oxide per mole of hydroxyl groups and bearing, as end group, a polymerizable unsaturated group, for instance a group of vinyl ether, allyl ether, acrylate ester or methacrylate ester type, and acrylate and methacrylate esters of polyols comprising at least two functional groups of acrylate or methacrylate ester type such as trimethylolpropane triacrylate (TMPTA), 15-ethoxylated trimethylolpropane triacrylate (TMPEO15TA), trimethylolpropane dimethacrylate, triethylene glycol dimethacrylate (TEGDMA) and bisphenol A dimethacrylate ethoxylated with 30 mol of ethylene oxide (EOBDMA). Ethoxylated polyols that may especially be mentioned include ethoxylated bisphenol A di(meth)acrylate, ethoxylated bisphenol F di(meth)acrylate and ethoxylated trimethylolpropane tri(meth)acrylate.

In a preferred variant of the invention, the anionic associative polymer(s) comprise, in addition to at least one unit of formula (I) and at least one unit of formula (II), at least one unit of formula (V) below:

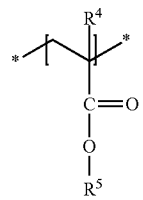

with $R^4$ representing a hydrogen atom or a methyl group, and
$R^5$ representing a $C_1$ to $C_4$ alkyl group, and in particular a methyl or ethyl group. Preferably, $R^5$ represents an ethyl group.

In a particularly preferred embodiment of this variant, the anionic associative polymer(s) preferably comprise at least one unit of formula (I) as defined above, at least one unit of formula (II') as defined above and at least one unit of formula (V) as defined above, with $R^1$ and $R^4$, independently of each other, representing a hydrogen atom or a methyl group, $R^3$ representing a $C_8$ to $C_{30}$ alkyl group, $R^5$ representing a $C_1$ to $C_4$ alkyl group, preferably an ethyl or methyl group, $M_1$ representing a hydrogen atom or a physiologically acceptable cation, and x being an integer ranging from 5 to 35 and preferably ranging from 10 to 24.

Preferably, $M_1$ represents a hydrogen atom, a sodium ion or an ion derived from an alkanolamine.

Preferably, an anionic associative polymer that is most particularly suitable for use in the composition according to the invention is the acrylate/steareth-20 methacrylate crosslinked copolymer (INCI name: acrylate/steareth-20 methacrylate crosspolymer) which comprises 20 ethylene oxide units. Such a polymer is sold, for example, by the company Röhm & Haas, in the form of a dispersion at 28-30% by weight in water, under the brand name Aculyn® 88.

The particular anionic associative polymer(s) (i) may represent from 0.1% to 20% by weight, preferably from 0.5% to 15% by weight, more preferentially from 1% to 10% by weight and in particular from 1% to 5% by weight, relative to the total weight of the composition.

As explained previously, the composition according to the invention also comprises one or more anionic fixing polymers (ii) comprising at least one unit of formula (III) and at least one unit of formula (IV) below:

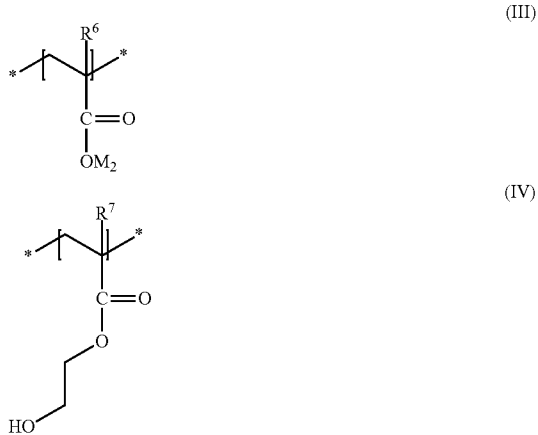

with $R^6$ and $R^7$, independently of each other, representing a hydrogen atom or a methyl group, and $M_2$ representing a hydrogen atom or a physiologically acceptable cation.

Preferably, $M_2$ represents a hydrogen atom, a sodium ion or an ion derived from an alkanolamine.

In a preferred variant of the invention, the anionic fixing polymer(s) comprise, in addition to at least one unit of formula (III) and at least one unit of formula (IV), at least one unit of formula (V) as defined above, with $R^4$ representing a hydrogen atom or a methyl group, and $R^5$ representing a $C_1$ to $C_4$ alkyl group, in particular a methyl, ethyl or n-butyl group.

These anionic fixing polymers (ii) are different from the anionic associative polymers (i).

Preferably, in the composition according to the invention, the anionic fixing polymer(s) are non-crosslinked.

Preferably, the anionic fixing polymer that may be used in the composition according to the invention is a copolymer of methacrylic acid/hydroxyethyl methacrylate and of at least one $C_1$ to $C_4$ (meth)acrylic acid ester.

In a most particularly preferred manner, the anionic fixing polymer that may be used in the composition according to the invention is a methacrylic acid/hydroxyethyl methacrylate/methyl methacrylate/butyl acrylate linear tetrapolymer.

Such a polymer is known especially under the trade name Acudyne® 180 and is sold by the company Röhm & Haas.

The anionic fixing polymer(s) (ii) may represent from 0.1% to 20% by weight, preferably from 0.2% to 15% by weight, more preferentially from 0.5% to 10% by weight and in particular from 1% to 8% by weight, relative to the total weight of the composition.

Preferably, in the composition according to the invention, the weight ratio of the anionic associative polymer(s) to the anionic fixing polymer(s) ranges from 0.2 to 5, preferably from 0.5 to 5 and in particular from 0.6 to 2.

As explained previously, the composition according to the invention also comprises one or more starches or modified starches (iii).

The starch(es) or modified starch(es) that may be used in the composition according to the invention are more particularly macromolecules in the form of polymers formed from elemental units that are anhydroglucose units. The number of these units and their assembly make it possible to distinguish amylose (linear polymer) and amylopectin (branched polymer). The relative proportions of amylose and of amylopectin, and their degree of polymerization, vary as a function of the plant origin of the starches.

The starch molecules used in the present invention may originate from a plant source such as cereals, tubers, roots, legumes and fruit. Thus, the starch(es) may originate from a plant source chosen from corn, pea, potato, sweet potato, banana, barley, wheat, rice, oat, sago, tapioca and sorghum. The starch is preferably derived from potato.

It is also possible to use the starch hydrolysates mentioned above.

Starches are generally in the form of a white powder, which is insoluble in cold water, whose elemental particle size ranges from 3 to 100 microns.

The starches used in the composition of the invention may be chemically modified via one or more of the following reactions: pregelatinization, oxidation, crosslinking, esterification, hydroxyalkylation and heat treatment.

More particularly, these reactions may be performed in the following manner:
  pregelatinization by splitting the starch granules (for example drying and cooking in a drying drum);
  oxidation with strong oxidizing agents, leading to the introduction of carboxyl groups into the starch molecule and to depolymerization of the starch molecule (for example by treating an aqueous starch solution with sodium hypochlorite);
  crosslinking with functional agents capable of reacting with the hydroxyl groups of the starch molecules, which will thus bond together (for example with glyceryl and/or phosphate groups);
  esterification in alkaline medium for the grafting of functional groups, especially $C_1$ to $C_6$ acyl (acetyl), $C_1$ to $C_6$ hydroxyalkyl (hydroxyethyl or hydroxypropyl), carboxymethyl or octenylsuccinic;
  hydroxyalkylation by treatment with an alkylene oxide.

Monostarch phosphates (of the type St-O—PO—$(OX)_2$), distarch phosphates (of the type St-O—PO—(OX)—O-St) or even tristarch phosphates (of the type St-O—PO—(O-St)$_2$) or mixtures thereof may especially be obtained by crosslinking with phosphorus compounds.

X in particular denotes alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

The phosphorus compounds may be, for example, sodium tripolyphosphate, sodium orthophosphate, phosphorus oxychloride or sodium trimetaphosphate.

Distarch phosphates or compounds rich in distarch phosphate will especially be used, for instance the products sold under the references Prejel VA-70-T AGGL (gelatinized hydroxypropyl cassava distarch phosphate), Prejel TK1 (gelatinized cassava distarch phosphate) and Prejel 200 (gelatinized acetyl cassava distarch phosphate) by the company Avebe, or Structure Zea from National Starch (gelatinized hydroxypropyl corn distarch phosphate).

In the composition according to the invention, the modified starch(es) may be chosen from amphoteric starches.

These amphoteric starches contain one or more anionic groups and one or more cationic groups. The anionic and cationic groups may be linked to the same reactive site of the starch molecule or to different reactive sites; they are preferably linked to the same reactive site. The anionic groups may be of carboxylic, phosphate or sulfate type, preferably carboxylic. The cationic groups may be of primary, secondary, tertiary or quaternary amine type.

The amphoteric starches are especially chosen from the compounds of formulae (VI) to (IX) below:

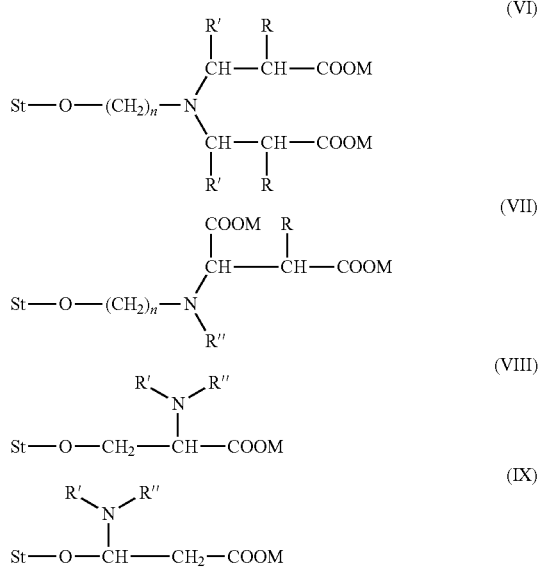

with St-O representing a starch molecule,

R, which may be identical or different in each formula, representing a hydrogen atom or a methyl radical, R', which may be identical or different in each formula, representing a hydrogen atom, a methyl radical or a —COOH group, n being an integer equal to 2 or 3, M, which may be identical or different in each formula, representing a hydrogen atom, an alkali metal or alkaline-earth metal such as Na, K, Li or $NH_4$, a quaternary ammonium or an organic amine, and R", which may be identical or different in each formula, representing a hydrogen atom or an alkyl radical containing from 1 to 18 carbon atoms.

These compounds are especially described in patents U.S. Pat. Nos. 5,455,340 and 4,017,460, which are included by way of reference.

The starches of formula (VI) or (VII) are particularly used as amphoteric starches. Starches modified with 2-chloroethylaminodipropionic acid are more particularly used, i.e. starches of formula (VI) or (VII) in which R, R', R" and M represent a hydrogen atom and n is equal to 2. Mention may be made in particular of the potato starch modified with 2-chloroethylaminodipropionic acid neutralized with sodium hydroxide, sold under the reference Structure Solanace by the company National Starch.

A modified starch that may also be mentioned is O-carboxymethyl starch.

The term "O-carboxymethyl starch" denotes a starch that has been modified by substitution, in free hydroxyl groups, of a hydrogen with a carboxymethyl group —$CH_2COOH$. It may be present as is, or in the form of a salt, for example an alkali metal salt.

O-Carboxylmethyl starches may be prepared, for example, by reacting a starch with monochloroacetic acid, or an alkali metal salt of monochloroacetic acid (for example the sodium salt).

Preferably, an O-carboxymethyl starch in the form of an alkali metal salt, and more preferably in the form of a sodium salt, is used.

Preferably, the O-carboxylmethyl starch is prepared from starch derived from potato.

The O-carboxymethyl starch may also be totally or partially crosslinked. Preferably, it is partially crosslinked. The crosslinking of the starch may be performed, for example, by heating the starch, or by reacting it with crosslinking agents such as phosphates or glycerol.

Even more preferably, the O-carboxymethyl starch is a partially crosslinked sodium salt of O-carboxymethyl potato starch. Such a product is sold, for example, under the name Primojel by the company Avebe.

Hydroxyalkyl starches that may be mentioned include starches treated with propylene oxide and in particular hydroxypropyl starches, such as the product sold under the reference Amaze by the company Akzo Nobel.

Preferably, in the composition according to the invention, the starch(es) or modified starch(es) are nonionic.

In a most particularly preferred manner, the modified starch(es) are chosen from starches treated with propylene oxide, and in particular are chosen from hydroxypropyl starches.

The starch(es) or modified starch(es) (iii) may represent from 0.01% to 10% by weight, preferably from 0.05% to 3% by weight and in particular from 0.1% to 1% by weight, relative to the total weight of the composition.

According to one embodiment, the composition according to the present invention comprises:
  i) one or more anionic associative polymers containing at least one unit of formula (I) as defined above, at least one unit of formula (II') as defined above and at least one unit of formula (III) as defined above,
  ii) one or more anionic fixing polymers containing at least one unit of formula (IV) as defined above, at least one unit of formula (V) as defined above and at least one unit of formula (III) as defined above,
  iii) one or more starches or nonionic modified starches.

In accordance with this embodiment, the fixing polymer is preferably a copolymer of methacrylic acid/hydroxyethyl methacrylate and of at least one $C_1$ to $C_4$ (meth)acrylic acid ester.

In accordance with this embodiment, the starch(es) are preferably chosen from starches treated with propylene oxide, and in particular are chosen from hydroxypropyl starches.

According to a preferred embodiment, the composition according to the present invention may also comprise one or more surfactants chosen from anionic surfactants, amphoteric or zwitterionic surfactants, nonionic surfactants and cationic surfactants.

The term "anionic surfactant" means a surfactant comprising, as ionic or ionizable groups, only anionic groups.

These anionic groups are preferably chosen from the groups $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2^-$, $PO_2^{2-}$, POH and $PO^-$.

As examples of anionic surfactants that may be used in the composition according to the invention, mention may be made of alkyl sulfates, alkyl ether sulfates, alkylamido ether sulfates, alkylarylpolyether sulfates, monoglyceride sulfates, alkylsulfonates, alkylamidesulfonates, alkylarylsulfonates, α-olefin sulfonates, paraffin sulfonates, alkylsulfosuccinates, alkylether sulfosuccinates, alkylamide sulfosuccinates, alkylsulfoacetates, acylsarcosinates, acylglutamates, alkylsulfosuccinamates, acylisethionates and $N-(C_1-C_4)$alkyl N-acyltaurates, salts of alkyl monoesters and of polyglycoside-polycarboxylic acids, acyllactylates, D-galactoside uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds (unless otherwise mentioned) generally comprising from 6 to 24 carbon atoms and the aryl group generally denoting a phenyl group.

These compounds can be oxyethylenated and then preferably comprise from 1 to 50 ethylene oxide units.

The salts of $C_6-C_{24}$ alkyl monoesters and of polyglycoside-polycarboxylic acids can be chosen from $C_6-C_{24}$ alkyl polyglycoside-citrates, $C_6-C_{24}$ alkyl polyglycoside-tartrates and $C_6-C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline-earth metal salts, in particular the sodium or magnesium salts.

The anionic surfactants that may be present may be mild anionic surfactants, i.e. anionic surfactants without a sulfate function.

Mention may in particular be made, as regards the mild anionic surfactants, of the following compounds and salts thereof, and also mixtures thereof:
polyoxyalkylenated alkyl ether carboxylic acids;
polyoxyalkylenated alkylaryl ether carboxylic acids;
polyoxyalkylenated alkylamido ether carboxylic acids, in particular those comprising 2 to 50 ethylene oxide groups;
alkyl-D-galactoside uronic acids;
acylsarcosinates, acylglutamates; and
alkylpolyglycoside carboxylic esters.

Use may be made most particularly of polyoxyalkylenated alkyl ether carboxylic acids, for instance lauryl ether carboxylic acid (4.5 OE) sold, for example, under the name Akypo RLM 45 CA from Kao.

The amphoteric or zwitterionic surfactant(s) that may be used in the present invention may especially be secondary or tertiary aliphatic amine derivatives, optionally quaternized, in which the aliphatic group is a linear or branched chain containing from 8 to 22 carbon atoms, the said amine derivatives containing at least one anionic group, for instance a carboxylate, sulfonate, sulfate, phosphate or phosphonate group.

Mention may be made in particular of $(C_8-C_{20})$alkylbetaines, sulfobetaines, $(C_8-C_{20})$alkylamido$(C_3-C_8)$alkylbetaines or $(C_8-C_{20})$alkylamido$(C_6-C_8)$alkylsulfobetaines.

Among the secondary or tertiary aliphatic amine derivatives, optionally quaternized, that may be used, as defined above, mention may also be made of the compounds of respective structures $(A_1)$, $(A_2)$ and $(A_3)$ below:

$$R_a-CONHCH_2CH_2-N^+(R_b)(R_c)(CH_2COO^-) \quad (A_1)$$

in which:
$R_a$ represents a $C_{10}-C_{30}$ alkyl or alkenyl group derived from an acid $R_a$—COOH preferably present in hydrolysed coconut oil, or a heptyl, nonyl or undecyl group,
$R_b$ represents a β-hydroxyethyl group, and
$R_c$ represents a carboxymethyl group;
and $$R'_a-CONHCH_2CH_2-N(B)(B') \quad (A_2)$$

in which:
B represents —$CH_2CH_2OX'$,
B' represents —$(CH_2)_z$—Y', with z=1 or 2,
X' represents the —$CH_2$—COOH, $CH_2$—COOZ', —$CH_2CH_2$—COOH or —$CH_2CH_2$—COOZ' group, or a hydrogen atom,
Y' represents —COOH, —COOZ', or the group —$CH_2$—CHOH—$SO_3H$ or $CH_2$—CHOH—$SO_3Z'$,
Z' represents an ion resulting from an alkali metal or alkaline-earth metal, such as sodium, an ammonium ion or an ion resulting from an organic amine,
$R'_a$ represents a $C_{10}$ to $C_{30}$ alkyl or alkenyl group of an acid $R'_a$—COOH which is preferably present in coconut oil or in hydrolysed linseed oil, or an alkyl group, especially a $C_{17}$ group, and its iso form, or an unsaturated $C_{17}$ group.

These compounds of formula $(A_1)$ or $(A_2)$ are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid.

By way of example, mention may be made of the cocoamphodiacetate sold by the company Rhodia under the trade name Miranol® C2M Concentrate.

$$R_a''-NHCH(Y'')-(CH_2)_nCONH(CH_2)_{n'}-N(R_d) \quad (A_3)$$
$$(R_e)$$

in which formula:
Y'' represents the group —COOH, —COOZ'', —$CH_2$—CH(OH)$SO_3H$ or the group —$CH_2CH(OH)SO_3$—Z'';
$R_d$ and $R_e$ represent, independently of each other, a $C_1-C_4$ alkyl or hydroxyalkyl radical;
Z'' represents a cationic counterion derived from an alkali metal or alkaline-earth metal, such as sodium, an ammonium ion or an ion derived from an organic amine;
$R_a''$ represents a $C_{10}-C_{30}$ alkyl or alkenyl group of an acid $R_a''$—COOH which is preferably present in coconut oil or in hydrolysed linseed oil;
n and n' denote, independently of each other, an integer ranging from 1 to 3.

Among the compounds of formula $(A_3)$, mention may be made of the compound classified in the CTFA dictionary under the name sodium diethylaminopropyl cocoaspartamide and sold by the company Chimex under the name Chimexane HB.

Among the abovementioned amphoteric or zwitterionic surfactants, it is preferred to use $(C_8-C_{20})$ alkylbetaines such as cocoylbetaine, ($C_8$-$C_{20}$) alkylamido($C_3$-$C_8$) alkylbetaines such as cocoylamidopropylbetaine, and mixtures thereof. More preferentially, the amphoteric or zwitterionic surfactant(s) are chosen from cocoylamidopropylbetaine and cocoylbetaine.

The nonionic surfactant(s) in the compositions of the present invention are especially described, for example, in the *Handbook of Surfactants* by M. R. Porter, published by Blackie & Son (Glasgow and London), 1991, pp. 116-178. They are especially chosen from fatty alcohols, fatty α-diols, fatty ($C_1$-$C_{20}$)alkylphenols and fatty acids, these compounds being ethoxylated, propoxylated or glycerolated and containing at least one fatty chain comprising, for example, from 8 to 18 carbon atoms, the number of ethylene oxide or propylene oxide groups possibly ranging especially from 1 to 200, and the number of glycerol groups possibly ranging especially from 1 to 30.

Mention may also be made of condensates of ethylene oxide and of propylene oxide with fatty alcohols, ethoxylated fatty amides preferably having from 1 to 30 ethylene oxide units, polyglycerolated fatty amides comprising on average from 1 to 5 glycerol groups, and in particular from 1.5 to 4, ethoxylated fatty acid esters of sorbitan containing from 1 to 30 ethylene oxide units, fatty acid esters of sucrose, fatty acid esters of polyethylene glycol, ($C_6$-$C_{24}$) alkylpolyglycosides, oxyethylenated plant oils, N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides.

The cationic surfactant(s) that may be used in the composition according to the invention are generally chosen from optionally polyoxyalkylenated primary, secondary or tertiary fatty amine salts, quaternary ammonium salts, and mixtures thereof.

Examples of quaternary ammonium salts that may especially be mentioned include:
those corresponding to the general formula (X) below:

in which the groups $R_8$ to $R_{11}$, which can be identical or different, represent a linear or branched aliphatic group comprising from 1 to 30 carbon atoms or an aromatic group, such as aryl or alkylaryl, at least one of the groups $R_8$ to $R_{11}$ comprising from 8 to 30 carbon atoms and preferably from 12 to 24 carbon atoms. The aliphatic groups can comprise heteroatoms, such as, in particular, oxygen, nitrogen, sulfur and halogens.

The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate, and $C_1$-$C_{30}$ hydroxyalkyl groups, $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Preference is given, among the quaternary ammonium salts of formula (X), on the one hand, to tetraalkylammonium chlorides, such as, for example, dialkyldimethylammonium or alkyltrimethylammonium chlorides in which the alkyl group comprises approximately from 12 to 22 carbon atoms, in particular behenyltrimethylammonium chloride, distearyldimethylammonium chloride, cetyltrimethylammonium chloride or benzyldimethylstearylammonium chloride, or also, on the other hand, to distearoylethylhydroxyethylmethylammonium methosulfate, dipalmitoylethylhydroxyethylammonium methosulfate or distearoylethylhydroxyethylammonium methosulfate, or also, finally, to palmitylamidopropyltrimethylammonium chloride or stearamidopropyldimethyl(myristyl acetate)ammonium chloride, sold under the name Ceraphyl® 70 by the company Van Dyk.

quaternary ammonium salts of imidazoline, for instance those of formula (XI) below:

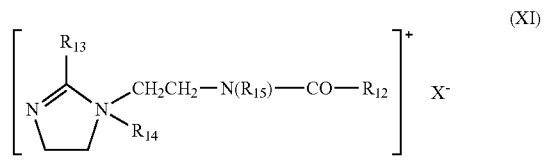

in which
$R_{12}$ represents an alkenyl or alkyl group comprising from 8 to 30 carbon atoms, for example derived from tallow fatty acids,
$R_{13}$ represents a hydrogen atom, a $C_1$-$C_4$ alkyl group or an alkenyl or alkyl group comprising from 8 to 30 carbon atoms,
$R_{14}$ represents a $C_1$-$C_4$ alkyl group,
$R_{15}$ represents a hydrogen atom, a $C_1$-$C_4$ alkyl group, $X^-$ is an anion chosen from the group of halides, phosphates, acetates, lactates, ($C_1$-$C_4$)alkyl sulfates and ($C_1$-$C_4$)alkyl- or ($C_1$-$C_4$)alkylarylsulfonates.

Preferably, $R_{12}$ and $R_{13}$ denote a mixture of alkenyl or alkyl groups comprising from 12 to 21 carbon atoms, for example derived from tallow fatty acids, $R_{14}$ denotes a methyl group and $R_{15}$ denotes a hydrogen atom. Such a product is sold, for example, under the name Rewoquat® W 75 by the company Rewo.

quaternary diammonium or triammonium salts, particularly of formula (XII) below:

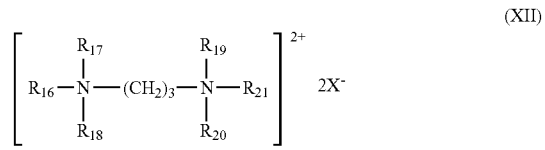

in which $R_{16}$ denotes an alkyl group comprising approximately from 16 to 30 carbon atoms, which is optionally hydroxylated and/or interrupted with one or more oxygen atoms, $R_{17}$ is chosen from hydrogen, an alkyl group comprising from 1 to 4 carbon atoms or a group —$(CH_2)_3$—$N^+(R_{16a})(R_{17a})(R_{18a})$, $R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms, and $X^-$ is an anion chosen from the group of halides, acetates, phosphates, nitrates, ($C_1$-$C_4$)alkyl sulfates, ($C_1$-$C_4$)alkyl- or ($C_1$-$C_4$)alkylarylsulfonates, in particular methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts comprising one or more ester functions, such as those of formula (XIII) below:

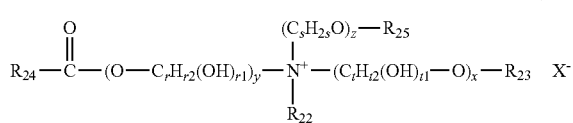
(XIII)

in which:

$R_{22}$ is chosen from $C_1$-$C_6$ alkyl groups and $C_1$-$C_6$ hydroxyalkyl or dihydroxyalkyl groups, $R_{23}$ is chosen from:
the group

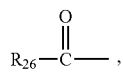

saturated or unsaturated and linear or branched $C_1$-$C_{22}$ hydrocarbon-based groups $R_{27}$,
a hydrogen atom, $R_{25}$ is chosen from:
the group

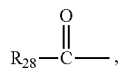

saturated or unsaturated and linear or branched $C_1$-$C_6$ hydrocarbon-based groups $R_{29}$,
a hydrogen atom, $R_{24}$, $R_{26}$ and $R_{28}$, which may be identical or different, are chosen from linear or branched, saturated or unsaturated $C_7$-$C_{21}$ hydrocarbon groups, r, s and t, which may be identical or different, are integers ranging from 2 to 6, r1 and t1, which are identical or different, have the values 0 or 1, r2+r1=2 r and t1+t2=2 t, y is an integer ranging from 1 to 10, x and z, which may be identical or different, are integers ranging from 0 to 10, $X^-$ is a simple or complex, organic or mineral anion, with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group and more particularly a methyl or ethyl group.

Advantageously, the sum x+y+z has a value from 1 to 10.

When $R_{23}$ is an $R_{27}$ hydrocarbon group, it can be long and have from 12 to 22 carbon atoms or be short and have from 1 to 3 carbon atoms.

When $R_{25}$ is an $R_{29}$ hydrocarbon group, it preferably has from 1 to 3 carbon atoms.

Advantageously, $R_{24}$, $R_{26}$ and $R_{28}$, which are identical or different, are chosen from saturated or unsaturated and linear or branched $C_{11}$-$C_{21}$ hydrocarbon groups and more particularly from saturated or unsaturated and linear or branched $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide, preferably chloride, bromide or iodide, a ($C_1$-$C_4$)alkyl sulfate or a ($C_1$-$C_4$)alkyl- or ($C_1$-$C_4$)alkylarylsulfonate. However, it is possible to use methanesulfonate, phosphate, nitrate, tosylate, an anion derived from an organic acid, such as acetate or lactate, or any other anion that is compatible with the ammonium containing an ester function.

The anion $X^-$ is more particularly still chloride, methyl sulfate or ethyl sulfate.

Use is made more particularly, in the composition according to the invention, of the ammonium salts of formula (XIII) in which:

$R_{22}$ denotes a methyl or ethyl group,
x and y are equal to 1,
z is equal to 0 or 1,
r, s and t are equal to 2,
$R_{23}$ is chosen from:
the group

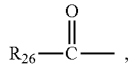

methyl, ethyl or $C_{14}$-$C_{22}$ hydrocarbon-based groups,
a hydrogen atom,
$R_{25}$ is chosen from:
the group

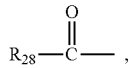

a hydrogen atom, $R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based groups are linear.

Among the compounds of formula (XIII), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil, such as palm oil or sunflower oil. When the compound comprises several acyl groups, the latter can be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts comprising at least one ester function described in patents U.S. Pat. Nos. 4,874,554 and 4,137,180.

Use may also be made of behenoylhydroxypropyltrimethylammonium chloride, for example, sold by the company Kao under the name Quartamin BTC 131.

Preferably, the ammonium salts comprising at least one ester function comprise two ester functions.

Among the cationic surfactants, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

Preferably, when they are present, the surfactant(s) are chosen from nonionic surfactants and cationic surfactants.

When the composition comprises one or more surfactants, their content may preferably range from 0.05% to 20% by weight, more preferentially from 0.1% to 10% by weight and better still from 0.5% to 5% by weight relative to the total weight of the composition.

The composition according to the invention may advantageously comprise one or more silicones or silicone derivatives, in soluble, dispersed or microdispersed form.

It may thus comprise one or more volatile or non-volatile silicones, which are non-organomodified or organomodified with organic groups especially such as amino groups, quaternized amino groups or thiol groups.

The composition according to the invention may also comprise fatty substances, which may be chosen especially from plant, mineral and synthetic oils, non-oxyalkylenated or non-glycerolated $C_{12}$-$C_{30}$ fatty alcohols, waxes and ceramides.

The composition according to the invention may also comprise one or more additives chosen from plasticizers, co-thickeners other than those described previously, sunscreens, antioxidants, acids, bases, fragrances, preserving agents, mineral fillers, nacreous agents, opacifiers, dyes and glitter flakes.

A person skilled in the art will take care to select the optional additives and the content thereof such that they do not harm the properties of the compositions of the present invention.

These additives may each be present in the composition according to the invention in a content ranging from 0 to 20% by weight, relative to the total weight of the composition.

Particularly preferably, the composition according to the invention also comprises water, which advantageously represents from 40% to 99% by weight, preferably from 50% to 95% by weight and better still from 55% to 80% by weight, relative to the total weight of the composition.

The composition can additionally comprise one or more water-soluble organic solvents (solubility of greater than or equal to 5% by weight in water at 25° C. and at atmospheric pressure).

Examples of water-soluble organic solvents that may be mentioned include linear or branched and preferably saturated monoalcohols or diols, comprising 2 to 10 carbon atoms, such as ethyl alcohol, isopropyl alcohol, hexylene glycol (2-methyl-2,4-pentanediol), neopentyl glycol and 3-methyl-1,5-pentanediol, butylene glycol, dipropylene glycol and propylene glycol; aromatic alcohols such as phenylethyl alcohol; polyols containing more than two hydroxyl functions, such as glycerol; polyol ethers, for instance ethylene glycol monomethyl, monoethyl or monobutyl ether, propylene glycol or ethers thereof, for instance propylene glycol monomethyl ether; and also diethylene glycol alkyl ethers, especially $C_1$ to $C_4$ alkyl ethers, for instance diethylene glycol monoethyl ether or monobutyl ether, alone or as a mixture.

The water-soluble organic solvents, when they are present, generally represent from 1% to 40% by weight and preferably from 5% to 35% by weight relative to the total weight of the composition.

Preferably, in the composition according to the invention, the pH ranges from 3 to 11 and preferably from 4 to 9.

The composition according to the invention may be in the form of liquids that are more or less thickened, gels, creams, pastes or foams.

Preferably, the composition according to the invention is provided in the gel form.

In a preferred alternative form, the viscosity of the compositions of the invention is greater than or equal to 0.1 Pa·s, better still greater than or equal to 0.2 Pa·s and even better still greater than or equal to 0.5 Pa·s at 25° C. and at a shear rate of 1 $s^{-1}$. This viscosity can be determined with a rheometer having cone-plate geometry.

A subject of the invention is also the use of the composition as defined previously for styling the hair.

Finally, a subject of the invention is a process for treating keratin fibres, preferably the hair, comprising the application of the composition as defined previously to the keratin fibres, with or without final rinsing after an optional leave-on time.

Preferably, the application of the compositions of the invention is a leave-on application.

The composition according to the invention may be applied at room temperature (25° C.) or with a supply of heat (from 45° C. to 230° C.).

The examples that follow are given purely as illustrations of the present invention.

EXAMPLES

Compositions A to E according to the invention and the comparative composition F were prepared from the ingredients given in the table below, in grams of starting material (active material in parentheses).

| Ingredients | A | B | C | D | E | F |
|---|---|---|---|---|---|---|
| Acrylates/Steareth-20 methacrylate crosslinked copolymer[1] | 6.9 (1.960 AM) | 8 (2.272 AM) | 4.5 (1.278 AM) | 5.7 (1.619 AM) | 8 (2.272 AM) | 8 (2.272 AM) |
| Acrylates/hydroxyacrylates copolymer[2] | 10 (4.725 AM) | 6 (2.835 AM) | 6 (2.835 AM) | 6 (2.835 AM) | 9 (4.252 AM) | 9 (4.252 AM) |
| Pregelatinized hydroxypropyl corn starch with a high content of amylose[3] | 0.5 (0.455 AM) | 0.5 (0.455 AM) | 1 (0.910 AM) | 1 (0.910 AM) | 0.5 (0.455 AM) | — |
| Copolymer of hexamethyl diisocyanate/polyethylene glycol bearing α, ω stearylpolyoxyethylene end groups[4] | — | — | — | — | — | 0.5 |
| Glycerol | — | 2 | — | — | — | — |
| Propylene glycol | 3 | — | — | — | 3 | 3 |
| Disodium salt of ethylenediaminetetraacetic acid | — | 0.1 | — | — | — | — |
| Sorbitol as an aqueous 70% solution | 2 (1.4 AM) | 2 (1.4 AM) | 3 (2.1 AM) | 2 (1.4 AM) | 2 (1.4 AM) | 2 (1.4 AM) |
| Methacrylic acid/methyl acrylate/ethoxylated dimethyl-meta-isopropenyl benzyl isocyanate alcohol terpolymer as a solution[5] | — | — | 1 (0.23 AM) | — | — | — |
| Vinylpyrrolidone/dimethylaminoethyl methacrylate copolymer at 20% in water | — | 14 (2.8 AM) | — | — | — | — |
| Oxyethylenated (40 EO) hydrogenated castor oil | 1 | 1 | 1 | 1 | 1 | 1 |
| 2-Methyl-4-isothiazolin-3-one at 9.5% in water | — | 0.1 (0.0095 AM) | — | 0.1 (0.0095 AM) | — | — |
| Polyethylene glycol (90 000 OE) | — | — | — | 0.2 | — | — |
| Triethanolamine | 2.5 | 2.5 | 2 | 1.5 | 2.5 | 2.5 |
| Ethanol | 2 | 2 | 18.6 | 2 | 2 | 2 |
| Fragrance | — | — | 0.4 | 0.2 | — | — |
| Preserving agents | 1 | 1 | — | 1.1 | 1 | 1 |
| 2-Amino-2-methyl-1-propanol | qs pH | qs pH | qs pH | qs pH | — | — |
| Deionized water | qs 100 g | qs 100 g | qs 100 g | qs 100 g | qs 100 g | qs 100 g |

[1] Aculyn ® 88 sold by the company Röhm & Haas
[2] Acudyne ® 180 sold by the company Röhm & Haas
[3] Amaze sold by the company Akzo Nobel
[4] INCI name: Steareth-100/PEG-136/HDI-trade name Rheolate ® FX 1100 sold by the company Elementis
[5] INCI name: Polyacrylate-3 sold under the name Viscophobe DB 1000 by Amerchol Compositions A to E according to the invention are in the form of a gel.

Compositions A to E according to the invention are used as styling gels.

Compositions A to E according to the invention have improved working qualities, and in particular easier uptake in the hands and better spreading in the hands, and also better distribution and good spreading of the gel onto the hair, when compared with the comparative composition F.

Furthermore, while preserving high styling performance qualities, i.e. good fixing and long-lasting hold of the hairstyle, compositions A to E according to the invention leave little or no residue on the surface of the hair.

The invention claimed is:

1. A composition comprising:

i) at least one anionic associative polymer, ii) at least one or anionic fixing polymer, iii) at least one starch or modified starch, the anionic associative polymer comprising at least one unit of formula (I) and at least one unit of formula (II) below:

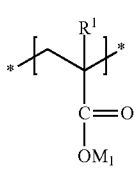

(I)

-continued

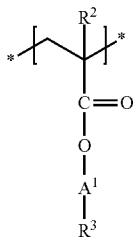
(II)

with R¹ and R², independently of each other, representing a hydrogen atom or a methyl group,
R³ representing a $C_8$-$C_{30}$ alkyl radical,
$M_1$ representing a hydrogen atom or a physiologically acceptable cation,
A¹ representing a group —$(CH_2CH_2O)_x$—, x being an integer ranging from 5 to 35, a group —$(CH_2CHMeO)_y$—, y being an integer ranging from 5 to 35, or a group —$(CH_2CH_2O)_x$—$(CH_2CHMeO)_y$—, the sum x+y being an integer ranging from 5 to 35 with x and y being greater than 0, and
the anionic fixing polymer comprising at least one unit of formula (III) and at least one unit of formula (IV) below:

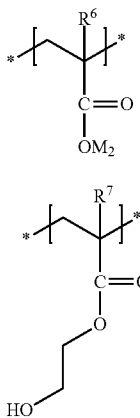
(III)

(IV)

with R⁶ and R⁷, independently of each other, representing a hydrogen atom or a methyl group, and
$M_2$ representing a hydrogen atom or a physiologically acceptable cation.

2. The composition according to claim 1, wherein the at least one anionic associative polymer is crosslinked.

3. The composition according to claim 1, wherein the at least one anionic associative polymer further comprises at least one unit of formula (V) below:

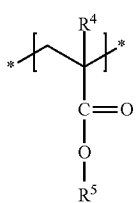
(V)

with R⁴ representing a hydrogen atom or a methyl group, and
R⁵ representing a $C_1$ to $C_4$ alkyl group, or methyl or ethyl group.

4. The composition according to claim 1, wherein the anionic associative polymer is present in an amount ranging from about 0.1% to about 20% by weight, relative to the total weight of the composition.

5. The composition according to claim 1, wherein the at least one anionic fixing polymer further comprises at least one unit of formula (V) below:

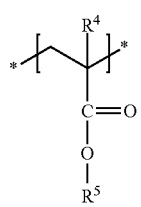
(V)

with R⁴ representing a hydrogen atom or a methyl group, and
R⁵ representing a $C_1$ to $C_4$ alkyl group, or a methyl, ethyl, or n-butyl group.

6. The composition according to claim 1, wherein the at least one anionic fixing polymer is non-crosslinked.

7. The composition according to claim 1, wherein the anionic fixing polymer is present in an amount ranging from about 0.1% A to about 20% by weight, relative to the total weight of the composition.

8. The composition according to claim 1, wherein the modified starch is chosen from starches that have undergone at least one of the following reactions: pregelatinization, oxidation, crosslinking, esterification, hydroxyalkylation, or heat treatment.

9. The composition according to claim 1, wherein the at least one starch or modified starch is nonionic.

10. The composition according to claim 1, wherein the modified starch is chosen from starches treated with propylene oxide or from hydroxypropyl starches.

11. The composition according to claim 1, wherein the least one starch or modified starch is present in an amount ranging from about 0.01% to about 10% by weight, relative to the total weight of the composition.

12. A method for the cosmetic treatment of keratinous fibers, in particular human keratinous fibers, the method comprising:
applying to the human keratinous fibers a composition comprising:
i) at least one anionic associative polymer,
ii) at least one or anionic fixing polymer,
iii) at least one starch or modified starch,
the anionic associative polymer comprising at least one unit of formula (I) and at least one unit of formula (II) below:

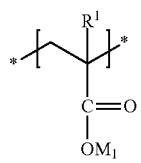
(I)

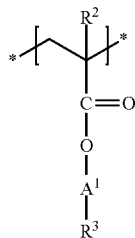
(II)

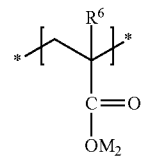
(III)

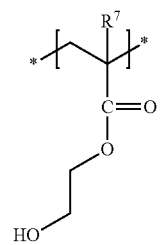
(IV)

with $R^1$ and $R^2$, independently of each other, representing a hydrogen atom or a methyl group, $R^3$ representing a $C_8$-$C_{30}$ alkyl radical, $M_1$ representing a hydrogen atom or a physiologically acceptable cation, $A^1$ representing a group —$(CH_2CH_2O)_x$—, x being an integer ranging from 5 to 35, a group —$(CH_2CHMeO)_y$—, y being an integer ranging from 5 to 35, or a group —$(CH_2CH_2O)_x$—$(CH_2CHMeO)_y$—, the sum x+y being an integer ranging from 5 to 35 with x and y being greater than 0, and the anionic fixing polymer(s) comprising at least one unit of formula (III) and at least one unit of formula (IV) below:

with $R^6$ and $R^7$, independently of each other, representing a hydrogen atom or a methyl group, and $M_2$ representing a hydrogen atom or a physiologically acceptable cation.

* * * * *

UNITED STATES PATENT AND TRADEMARK OFFICE
CERTIFICATE OF CORRECTION

PATENT NO. : 10,517,811 B2
APPLICATION NO. : 15/100788
DATED : December 31, 2019
INVENTOR(S) : Anne-Sophie Brac De La Perriere et al.

Page 1 of 1

It is certified that error appears in the above-identified patent and that said Letters Patent is hereby corrected as shown below:

In the Claims

Column 22, Claim 7, Line 31, after "0.1%" please remove "A".

Signed and Sealed this
Third Day of March, 2020

Andrei Iancu
*Director of the United States Patent and Trademark Office*